United States Patent [19]

Shaw et al.

[11] Patent Number: 4,846,826
[45] Date of Patent: * Jul. 11, 1989

[54] METHOD FOR TREATING ISCHEMIC CONDITIONS

[75] Inventors: Jane Shaw, Atherton; Robert M. Gale, Mountain View, both of Calif.

[73] Assignee: Alza Corporation, Palo Alto, Calif.

[*] Notice: The portion of the term of this patent subsequent to Dec. 4, 2001 has been disclaimed.

[21] Appl. No.: 933,714

[22] Filed: Nov. 21, 1986

Related U.S. Application Data

[63] Continuation of Ser. No. 463,593, Feb. 3, 1983, Pat. No. 4,650,484, which is a continuation of Ser. No. 285,862, Jul. 22, 1981, abandoned.

[51] Int. Cl.$^4$ .......................... A61K 9/00; A61K 9/22
[52] U.S. Cl. ................... 604/890.1; 424/461; 424/468
[58] Field of Search .............. 604/890–897; 424/19–24, 461–468

[56] References Cited

U.S. PATENT DOCUMENTS

| 2,896,819 | 7/1975 | Zaffaroni | 128/130 |
| 3,028,307 | 4/1962 | Ninger | 167/82 |
| 3,063,900 | 11/1962 | Winsor | 167/65 |
| 3,096,242 | 7/1963 | Young | 167/65 |
| 3,428,728 | 2/1969 | Lowey | 424/14 |
| 3,742,951 | 7/1973 | Zaffaroni | 128/268 |
| 3,789,119 | 1/1974 | Fusari et al. | 424/78 |
| 3,797,494 | 3/1974 | Zaffaroni | 128/268 |
| 3,921,636 | 11/1975 | Zaffaroni | 128/260 |
| 3,948,262 | 4/1976 | Zaffaroni | 128/260 |
| 3,977,982 | 8/1976 | Hertl | 436/16 |
| 3,980,084 | 9/1976 | Kross | 128/263 |
| 3,996,634 | 12/1976 | Zaffaroni | 128/268 |
| 4,014,335 | 3/1977 | Arnold | 128/260 |
| 4,031,894 | 6/1977 | Urquhart et al. | 128/268 |
| 4,060,084 | 11/1977 | Chandrasekaran et al. | 128/260 |
| 4,286,692 | 9/1981 | Chandrasekaran | 128/260 |
| 4,329,333 | 5/1982 | Barr | 424/19 |
| 4,350,785 | 9/1982 | Habib | 524/55 |
| 4,384,398 | 3/1983 | Shaw et al. | 604/897 |
| 4,486,193 | 12/1984 | Shaw et al. | 604/897 |
| 4,615,699 | 10/1986 | Gale et al. | 604/897 |
| 5,262,003 | 4/1981 | Urquhart et al. | 128/260 |

FOREIGN PATENT DOCUMENTS 0013606 7/1980 European Pat. Off. .

OTHER PUBLICATIONS

Boehm, *Angewandte Chemie*, vol. 5, pp. 533, 538–541, 1966.
Cabot, Advertisements, pp. 4, 9, 12 and 18, 1979.
Parkyns, *Cata. Proc. Int. Congr.* 5th, vol. 12, pp. 255 & 261, 1973.
Goodman, *The Pharmacological Basis of Therapeutics*, 4th Ed., p. 752, 1970.
Burch, *Am. Heart J.*, p. 842, 1966.
Csaky, *Handbook of Pharmacology*, 6th Ed., pp. 241–243, 1979.
Banes, *J. Pharm. Sci.*, vol. 57, pp. 893–894, 1968.
Merck, *The Merck Index*, p. 965, 1968.
Pauling, *The Nature of the Chemical Bond*, p. 495, 1960.

Primary Examiner—Barry S. Richman
Assistant Examiner—T. J. Wallen
Attorney, Agent, or Firm—Paul L. Sabatine; Edward L. Mandell; Steven F. Stone

[57] ABSTRACT

A method is disclosed for treating an ischemic condition. The method comprises coadministering topically and internally a vasodilator to a patient having the condition for treating the condition.

3 Claims, 1 Drawing Sheet

METHOD FOR TREATING ISCHEMIC CONDITIONS

CROSS-REFERENCE TO RELATED APPLICATIONS

This application is a continuation of U.S. patent application Ser. No. 06/463,593 filed on Feb. 3, 1983, now U.S. Pat. No. 4,650,484 which application Ser. No. 06/463,593 is a continuation of U.S. patent application Ser. No. 06/285,862 filed on July 22, 1981 now abandoned. These applications are incorporated herein by reference and benefit is claimed of their filing dates. These applications are assigned to ALZA Corporation of Palo Alto, Calif.

FIELD OF THE INVENTION

This invention pertains to a method for the management of ischemic conditions including angina pectoris by administering topically and internally a vasodilator drug to a symptomatic patient.

BACKGROUND OF THE INVENTION

Vasodilator drugs are the mainstay in the symptomatic treatment of ischemic conditions including angina pectoris. Patients afflicted with these conditions, especially angina pectoris, may require almost immediate therapeutic response to a vasodilator drug for relief from pain, and in some instances fright, or patients with angina pectoris may require a continuous therapeutic response to a vasodilator drug to decrease the frequency and severity of attacks. Consequently, vasodilator drugs frequently are administered sublingually because this method provides a rapid onset of therapeutic effect and accompanying immediate relief of symptoms; also vasodilator drugs are frequently administered orally because this method provides a longer duration of action for alleviating clinical symptoms and can provide prophylactic benefit.

While the above methods of administration provide needed benefits, there are disadvantages associated therewith. For example, sublingually administered vasodilator drugs have a brief duration of action making it necessary for some patients to take many doses, and orally administered vasodilator drugs often are used in high doses, they are erratically absorbed into the systemic circulation, and do not provide continuous therapy.

OBJECTS OF THE INVENTION

Accordingly, it is an immediate object of this invention to provide both a novel and useful method for treating ischemic conditions including angina pectoris, which method overcomes the disadvantages known to the prior art.

Another object of the invention is to provide a method for treating ischemic conditions including angina pectoris, which method comprises a combination of administering a vasodilator drug topically and internally to a patient in need of such treatment.

Another object of the invention is to provide a method for treating ischemic conditions including intractable angina pectoris which method comprises administering a vasodilator drug topically and concomitantly internally to produce clinically satisfactory results.

Yet still another object of this invention is to provide a method for treating angina pectoris in a human afflicted with same by administering a vasodilator drug or different vasodilator drugs topically and simultaneously internally for obtaining clinical and therapeutic efficacy in treating angina pectoris.

Yet another object of this invention is to provide a method for lessening the incidence of anginal attacks by administering at least one vasodilator drug in a therapeutically effective amount topically and internally for producing the intended result.

Other objects features and advantages of this invention will be more apparent to those skilled in the art from the detailed description of the invention, and the accompanying claims.

DETAILED DESCRIPTION OF THE INVENTION

Figure 1:
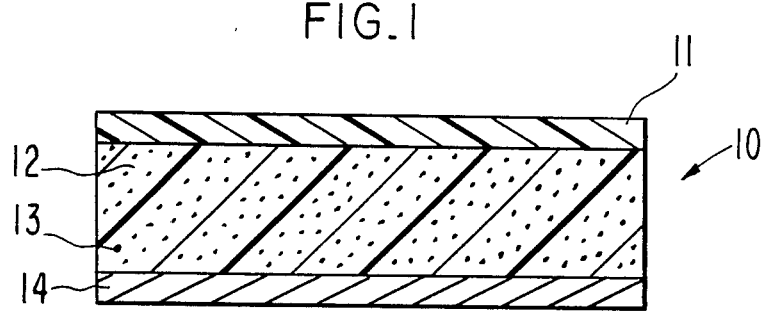
FIGS. 1, 2, and 3 show bandages according to the invention.

In accordance with the practice of the invention, there is provided a method comprising administering a vasodilator drug in a therapeutically effective and beneficial amount both topically and internally to a human patient over time. The method comprises coadministering the vasodilator simultaneously topically and internally, topically then internally, internally then topically, multiple administrations topically and internally, multiple administrations internally and topically, and the like.

The term topically as used herein, denotes administering to the skin of a patient in need of a vasodilator drug, the drug for percutaneous passage of the vasodilator into the systemic circulation of the patient. The skin sites include anatomic regions for transdermally administering the drug as represented by the forearm, abdomen, chest, back, buttock, mastoidal area and the like. The vasodilator is administered to the skin by placing on the skin a bandage that administers the vasodilator, and which bandage is designed, shaped, sized, and adapted for easy placement and comfortable retention on the skin.

The term internally as used herein, denotes administering the vasodilator orally into the gastrointestinal tract, administering the vasodilator into the mouth such as buccally to the inner surface of the cheeks, and sublingually beneath the tongue. The vasodilator can be administered internally in pharmaceutical formulations expressed as tablet, sustained release, pellet, capsule, solution, suspension, and the like.

The phrase vasodilator drug, and the term vasodilator as used herein denotes vasodilators including nitrites, nitrates and their esters, such as their esters of sugars and polyols. The vasodilators generically possess a member selected from the group consisting of ONO, and $ONO_2$. The vasodilators include amyl nitrite, ethyl nitrite, glyceryl trinitrate, also known as nitroglycerin, nitroglycerin absorbed on lactose such as 1 to 30% nitroglycerin on 99 to 70% lactose, preferably 10% nitroglycerin and 90% beta-lactose, or optionally on alpha-lactose, octyl nitrite, sodium nitrite, clonitrate, erythrityl tetranitrate, isosorbide dinitrate, mannitol hexanitrate, pentaerythritol tetranitrate, penetrinitol, triethanolamine trinitrate, trolnitrate phosphate (triethanolamine trinitrate diphosphate), propatylnitrate, and the like.

The expression ischemic conditions as used herein generically denotes conditions that respond to vasodilator therapy through hemodynamic response and the like. The condition includes vasodilators used to relieve pain in the treatment of its most common clinical expression angina pectoris, as a prophylactic for the prevention of angina pectoris and in hypertension, for the relaxation of the involuntary muscles of the blood vessels mainly the arteries and arterioles, for increasing oxygenation from vasodilation, mainly for increasing the supply of oxygen to the heart, for improving exercise performance, in the pharmaco-prevention of coronary disease, for increasing the circulation in the vascular bed for warming cold fingers and toes and for treating frostbite. The vasodilators and their uses are known in *Cutting's Handbook of Pharmacology*, Sixth Edition, Chapter 24, 1979, published by Appleton-Century-Crofts, New York.

Figure 2:
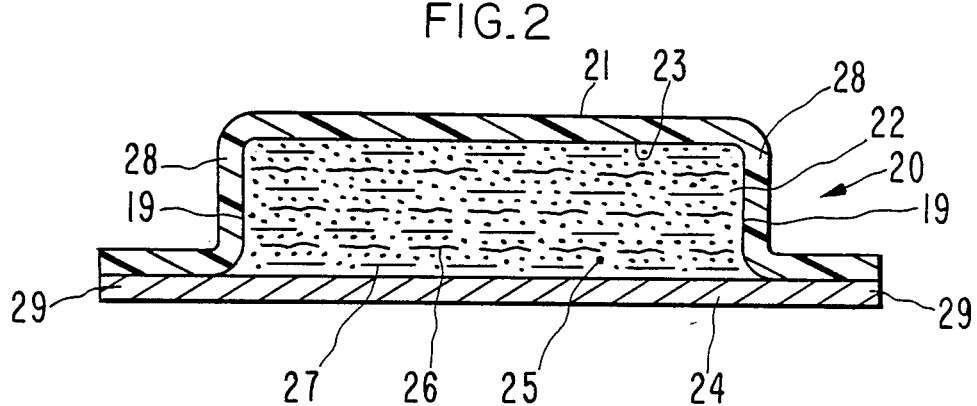
Figure 3:
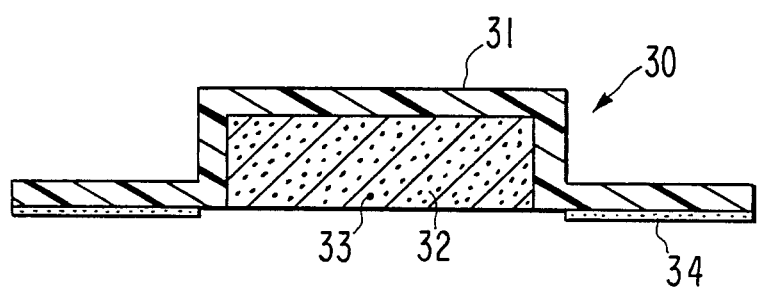

The medical bandage useful for the present purpose can have various shapes, such as oblong, square, round, rectangular, and the like. Medical bandages that can be used for the present purpose are seen in FIGS. 1, 2 and 3. In FIG. 1, medical bandage 10 is seen in opened section, and it comprises a backing member 11 that defines one face of bandage 10, and a reservoir 12, containing vasodilator drug 13. Reservoir 12 has a surface in contact with backing member 11 and a surface in contact with release rate controlling membrane 14. Backing member 14 is formed of occlusive or nonocclusive materials, and it is essentially impermeable to passage of components contained in bandage 10. Reservoir 12 is a mass transfer conductor and it is formed of a material that can contain from 5 mg to 750 mg of vasodilator to rate controlling membrane 14 for release of vasodilator 13 from device 10. Materials suitable for forming reservoir 12 include solid materials such as synthetic and naturally polymeric materials, including polyolefins, polyacrylic acids, polysilicones, copolymers of olefins, esters of olefinic acids, waxes and the like. Rate controlling membrane 14 is formed of a material that permits the passage of drug by diffusion, or it is formed of a microporous material. Materials that permit the passage of vasodilator drugs include polymers such as polyolefins, polydimethylsiloxanes, copolymers of ethylene-vinyl acetate, microporous polycarbonates, microporous polysulfones, and the like. The bandage is used by applying it directly to the skin for releasing a therapeutically effective amount of vasodilator to the skin. The bandage can be held on the skin by a thin film of non-toxic adhesive, by adhesive along the perimeter of the release rate membrane, or by mechanical means such as taping it to the skin. Procedures for manufacturing the medical bandage are disclosed in U.S. Pat. No. 3,598,122; 3,742,951; 3,996,934; and 4,031,894.

Another medical bandage that can be used for the present purpose is seen in FIG. 2. In FIG. 2, bandage 20 is seen in opened section, and it comprises a backing member 21 that serves as a protective cover and it is made of a material, or a combination of materials, or a laminate, which in any instance is impermeable to the passage of components in bandage 11. Typical materials for forming backing member 21 include high density polyethylene, metal foil, a laminate of a lamina of polyethylene in laminar arrangement with a lamina of aluminized polyethylene-terephthalate and a lamina of ethylene-vinyl acetate copolymer, or a laminate comprising a lamina of aluminized polyethylene-terephthalate, a lamina of ionomer and a lamina of ethylene-vinyl acetate copolymer.

A reservoir 22 is adjacent to backing member 21 and immediately below one surface 23 of backing member 21. Reservoir 22 bears on its surface distant from backing member 21 a membrane 24 for controlling the release of vasodilator drug 25 from medical bandage 20. Reservoir 22 is formed of a gelled fluid 26 having a low to high viscosity. Reservoir 22 is preferrably made as a continuous phase and it contains rheology agent 27 with vasodilator dispersed throughout the reservoir. In bandage 20, outer edges 28 of backing member 21 can overlay edges 19 of reservoir 22 and in this manufacture they will join edges 29 of membrane 24 in fluid tight arrangement. The sealed reservoir is made by pressure sealing, fusion, adhesion, or through an adhesive applied to the edges of contacting members. Medical bandage 20 is held on the skin of a human by a layer of adhesive, or optionally an adhesive that extends around the outer perimeter of membrane 24, or by mechanical means such as a strip of tape. Reservoir 22 contains about 5 to 750 mg of vasodilator, that is supplied in a dosage unit amount of drug 25 to release rate controlling membrane 24 throughout the medical history of bandage 20.

Generally, the dosage amount in a medical bandage used for the present purpose comprises a supply of vasodilator for one hour, for four hours, for eight hours for a normal night sleep, for 24 hours applied once daily, for 48 hours or longer, and the like. In practicing the invention, one or more than one bandage can be on the skin at the same time, and the bandages can be applied one after another.

Reservoir 22 comprises a gelled fluid, which latter term includes naturally occurring and synthetic oils. The oils are selected from the group consisting essentially of inorganic and organic oils, such as mineral, nut, plant, sylvan and vegetable oils. In a preferred embodiment silicone fluid, also called silicone oils, is used for forming the reservoir. The silicone fluids have a range of viscosities from 1 to 100,000 centistokes. Representative silicone fluids include dimethylsilicone fluid, methlphenylsiloxysilicone fluid, diphenylsiloxysilicone fluid, methylvinylsiloxysilicone fluid, polydimethylsiloxane fluid, and the like. Reservoir 22 contains a rheological agent that imparts gelling properties to the fluid. The rheologic agents are selected from cellulosic, polysaccharide and silicone agents. The polysaccharides include linear or branched polysaccharides such as agar, agarose, algin, sodium alginate, carrageenan, gum tragacanth, and the like. The cellulose agents include cellulose, cellulose derivatives, alkylcellulose, hydroxyalkylcellulose derivatives where the alkyl group is 1 to 7 carbons, carboxyalkylcellulose and the like. The silicone agents include fumed silica, precipitated silica, amorphous silica, colloidal silicon dioxide, fused silica, silica gel, and the like.

Release rate controlling membrane 24 is formed of polymers including polyolefins, polyamides, polyesters, ethylene-ethacrylate copolymer, segmented copolymer of butylene terephthalate 33% and polytetramethylene ether terephthalate 67%, segmented copolymer of propylene terephthatate 58% and polytetramethylene ether terephthalate, block copolymer of tetramethylene terephthalate-polytetramethylene ether glycol terephthalate, ethylene-vinyl acetate copolymer, and the like. In an embodiment the bandage is provided with a protective cover held in contact by an adhesive with the reservoir. The cover is stripped from the bandage before it is positioned on the skin, whereon it administers from 10 μg to 400 μg of vasodilator per hour.

Another bandage that can be used for administering a vasodilator topically is seen in FIG. 3. In FIG. 3, medical bandage 30 is seen in cross-section and it comprises a backing member 31, a reservoir 32 containing vasodilator 33 and an optional film of adhesive 34 for securing bandage 30 on a patient. Backing member 31 can be aluminium foil, polyethylene, Mylar ® polyethylene terephthalate, a laminate of polyethylene terephthalate with an intermediate layer of aluminum foil and a layer of ionomer, Surlyn ®, and the like. The same materials used for forming backing member 31 also can be used as a strippable cover, not shown, positioned over the reservoir and stripped free of bandage 30 before use. Reservoir 30 comprises glycerol, polyvinyl alcohol, a water soluble polymer with hydration sites selected from the group consisting of polyvinylpyrrolidone, agar, agarose and cellulose derivatives, water, 40 to 60 mg of trinitroglycerol as the lactose triturate, for releasing 5 mg of vasodilator over a 24 hour period. The medical bandage is held in place by, for example, silicone adhesive, an elastic band, and the like.

The pharmaceutical preparations for internal use include oral, sublingual and buccal dosage forms. The orally administered vasodilators include physiologically active vasodilators such as isosorbide dinitrate, nitroglycerin, pentaerythritol tetranitrate and the like. They can be used in dosage forms including capsules, tablets and sustained release forms. For example, isosorbide dinitrate can be made into capsules, timed release, containing 10 to 40 mg. tablets 5 to 20 mg and tablets, timed release 40 mg; erythrityl tetranitrate into tablets containing 5 to 15 mg; pentaerythritol tetranitrate as capsules, timed release, containing 30 and 80 mg and as tablets containing 10 and 20 mg; and nitroglycerin in capsules, plain and timed release 2.5, 6.5 and 9 mg and tablets 2.5 and 6.5 mg. For sublingual administration nitroglycerin is administered in doses up to 0.6 mg; for sublingual administration of isosorbide dinitrate the dose is 2.5 to 5 mg; and erythrityl tetranitrate the dose is 5 to 15 mg. Buccal administration uses a dosage corresponding to sublingual administration for passing through the mucosa and into the systemic circulation. The dosage form can be administered in a single dose, in more than one dose by the same or different internal routes, and in additional doses at successive intervals.

The dosage forms are made by standard manufacturing procedures. For example, tablets are made by standard procedures such as mixing a vasodilator such as nitroglycerin, inositol hexanitrate or the like with mannitol and magnesium stearate, and then compressing the mixture into tablets. A sustained release vasodilator medication is made by forming pellets of between 8 and 40 mesh size of an innocuous exipient such as milk sugar, mannitol, sorbitol and the like, and then coating the pellets with a vasodilator such as nitroglycerin, mannitol hexanitrate, erythritol tetranitrate, pentaerythritol or the like. The pellets and the vasodilator are mixed in a volatile liquid such as acetone, ether or the like, and the liquid then evaporated, to yield coated particles. The relative proportions of the pellets and medicament can vary, but generally about 1 part pellet to 3 parts of medicament can be used for making the pharmaceutical composition. Next, a disintegratable coating such as shellac, beeswax or the like is coated onto the medicament-pellets from an organic solvent such as acetone, and the coated sustained release form placed in an oven to dry. Next, some of sustained release coated pellets are mixed with pellets free of the disintegratable coating and charged into a gelatin capsule to provide both immediate and sustained release therapy. Internal dosage forms and procedures for making dosage forms are described in *Int. J. Pharm.*, Vol. 1, pages 197 to 204, 1978; *The Am. J. of Med.*, Vol. 65, pages 58 to 62, 1978; *AMA Drug Evaluations*, pages 529 to 532, 1980; *Remington's Pharmaceutical Science*, 14th Edition, pages 1649 to 1698, 1970; and, U.S. Pat. No. 2,963,402.

The method of administering a vasodilator topically from a transdermal therapeutic delivery system and internally from a pharmaceutical dosage form was demonstrated by the following study. The study was carried out with 13 male patients with chronic, stable angina pectoris due to arteriosclerotic heart disease. Eight of the patients suffered a myocardial infarction before the study. The patients had the disease for an average of 4 years and an average of 18 anginal attacks per week. The patients had an average age of 55 years, an average height of 168 cm and and average weight of 73 kg. The transdermal delivery system used for the study comprised an occlusive backing member, a reservoir adjacent to the backing member comprising gelled, medical silicone fluid, national formulary colloidal silicon dioxide and nitroglycerin-lactose, a lamina adjacent to the reservoir comprising release rate controlling ethylene-vinyl acetate copolymer having a vinyl acetate content of 9%, and an adhesive for holding the system on the skin. The systems delivered 40 $\mu g/hr/cm^2$ of nitroglycerin. Placebo systems were identical with nitroglycerin systems.

The study was conducted as a double-blind randomized cross-over comparison of the nitroglycerin system and the placebo system. The treatment schedule comprised a group of 7 patients using the placebo systems for weeks 1 and 2 and then crossing over and using a nitroglycerin system for weeks 3 and 4, and a second group of 6 patients using the nitroglycerin system for weeks 1 and 2 and then crossing over and using a placebo system for weeks 3 and 4. The patients were given weekly check-ups and also underwent exercise tests. The exercise testing followed the procedure reported in *Ann. Clin. Res.*, Vol. 3, pages 323 to 332, 1971. At the initial consultations, the study proper commenced, the patients were subjected to progressively increasing work-loads until angina was provoked. All subsequent exercise tests were performed at the same work-loads and under the same conditions.

The results of the study indicated, in all patients, anginal attacks were on the average of 60% less frequent during their 14 day period of treatment with system releasing nitroglycerin, than during the placebo period. Nitroglycerin was administered internally, sublingually in tablets containing up to 0.6 mg during the placebo and medication periods in response to anginal attacks. The results indicated patients took on the average greater than 2 tablets of nitroglycerin daily during the placebo period, and an average of less than 1 tablet of nitroglycerin daily during the medication period. The treatment with transdermal delivery of nitroglycerin and internally administered nitroglycerin lessen internal administrations on the average 63% when compared with the placebo period. Under medication, systolic blood pressure during exercise was lowered by 7 to 15 mmHg and diastolic pressure by 5 to 8 mmHg, heart rate immediately after exercise was also 3 to 11 beats/minute less than during placebo medication, and anginal attacks were less severe and of shorter duration.

While there has been described and pointed out features of the invention as applied to presently preferred embodiments, those skilled in the art will appreciate that various modifications, changes, additions and omissions of the method illustrated and described can be made without departing from the spirit of the invention.

We claim:

1. A method for treating angina in a patient having angina by transdermally and sublingually administering a drug to said patient for treating angina, wherein the method comprises:
   (a) placing on the dermis of patient afflicted with angina a medical bandage comprising:
      (1) a reservoir comprising a gel composition comprising: (i) an oil selected from the group consisting of an inorganic oil and an organic oil, (ii) a cellulosic means for gelling the oil, and (iii) a drug present in a therapeutically effective amount for treating angina;
      (2) a membrane adjacent to one surface of the reservoir, the membrane comprising a composition that aids in releasing the drug from the reservoir over time;
      (3) a backing member comprising a composition that is substantially impermeable to the passage of drug adjacent to the opposite surface of the reservoir, which backing contacts the membrane;
   (b) admitting sublingually into the patient a pharmaceutical dosage form comprising a drug useful for treating angina; and,
   (c) concomitently administering the drug transdermally for treating angina in the patient.

2. A method for treating angina in a patient having angina by transdermally and sublingually administering a drug for treating angina to said patient, which method comprises:
   (a) placing on the dermis of a patient afflicted with angina a medical bandage comprising:
      (1) a reservoir comprising a gel composition comprising: (i) an oil selected from the group consisting of an inorganic oil and an organic oil, (ii) a polysaccharide means for gelling the oil, and (iii) a drug present in a therapeutically effective amount for treating angina;
      (2) a membrane adjacent to one surface of the reservoir, the membrane comprising a composition that aids in releasing the drug from the reservoir over time;
      (3) a backing member comprising a composition that is substantially impermeable to the passage of drug, and is in contacting relation with the membrane;
   (b) admitting sublingually into the patient a pharmaceutical dosage form comprising a drug useful for treating angina; and,
   (c) successively administering the drug transdermally for treating angina in the patient.

3. A method for treating angina in a patient having angina, which method comprises:
   (a) administering to the patient sublingually a dosage form comprising a beneficial drug useful for treating angina;
   (b) administering to the patient transdermally from a medical bandage a drug useful for treating angina, which bandage comprises:
      (1) a backing member comprising a composition that is substantially impermeable to the passage of drug;
      (2) a reservoir in contact with the backing member, the reservoir comprising: a gel composition comprising silicone fluid, silicon dioxide and a drug useful for treating angina dispersed through the gel composition;
      (3) a membrane positioned opposite the backing member and adjacent to the reservoir, the membrane comprising a composition that aids in releasing drug from the reservoir and is in contact with the backing member; and,
   (c) wherein the drug is administered sublingually and transdermally in a therapeutically effective amount to the patient for treating angina.

* * * * *